United States Patent [19]

Raulerson

[11] 4,037,599
[45] July 26, 1977

[54] CONTINUOUS FLOW CATHETER DEVICE

[76] Inventor: James D. Raulerson, Rte. 2, Box 104, Alachua, Fla. 32615

[21] Appl. No.: 652,288

[22] Filed: Jan. 26, 1976

[51] Int. Cl.² .............................................. A61M 5/00
[52] U.S. Cl. .................................. 128/214.4; 128/240
[58] Field of Search ............. 128/214.4, 214.2, 214 R, 128/347, 348, 213, DIG. 16

[56] References Cited

U.S. PATENT DOCUMENTS

| | | | |
|---|---|---|---|
| 3,520,298 | 7/1970 | Lange | 128/213 |
| 3,670,729 | 6/1972 | Bennett et al. | 128/240 X |
| 3,827,434 | 8/1974 | Thompson et al. | 128/214.4 |
| 3,848,592 | 11/1974 | Willock | 128/214 R |

Primary Examiner—Stephen C. Pellegrino
Attorney, Agent, or Firm—Duckworth, Hobby, Orman, Allen & Pettis

[57] ABSTRACT

A catheter device used in the catherization of a blood vessel during hemodialysis which comprises a hub assembly having at least a first and second fluid conduit each of which are connected in fluid communication with separate concentrically disposed tube elements so as to define a first and second fluid flow path. The concentrically arranged tube elements provide for a single puncture into the predetermined blood vessel wherein the first and second fluid conduits are interconnected to a continuous negative and positive source of fluid flow so that blood will be continuously drawn from and supplied to the predetermined blood vessel by means of the outer and inner tube elements respectively. The hub assembly may comprise at least two hub portions correspondingly dimensioned and configured to define the two fluid conduits therein and also provide structure for securing the inner and outer tube elements to the hub assembly and further provide alignment structure for properly positioning the two hub portions into mating engagement with one another to define the operative hub assembly.

17 Claims, 10 Drawing Figures

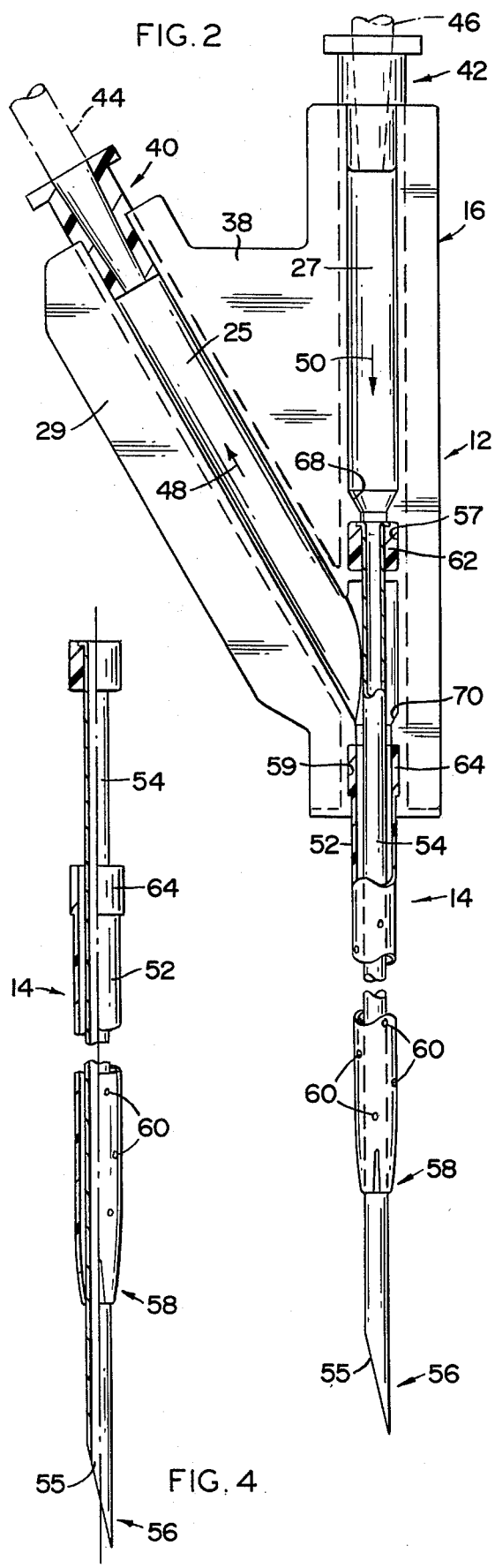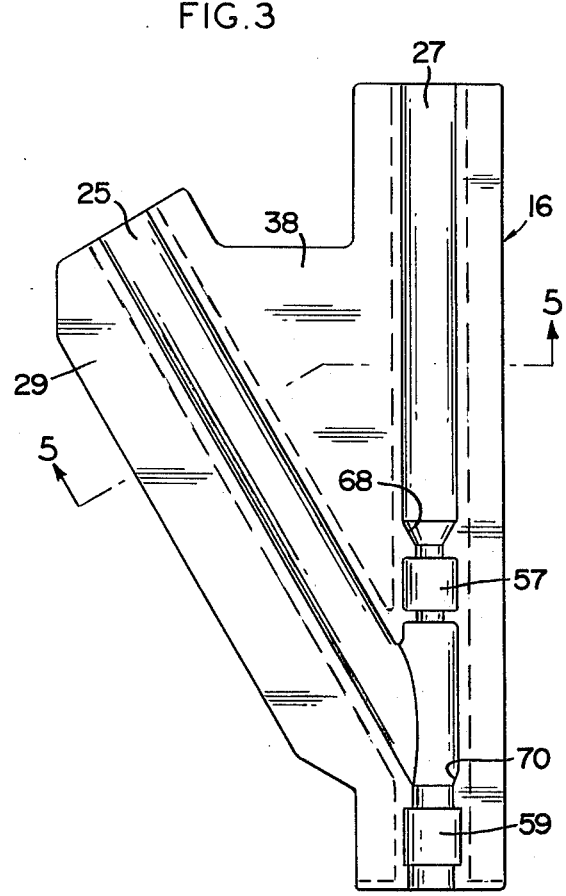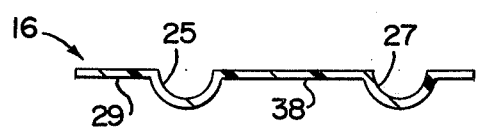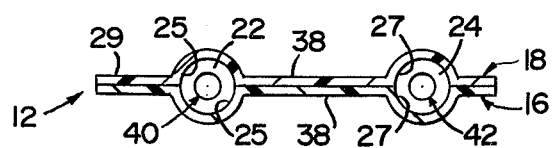

CONTINUOUS FLOW CATHETER DEVICE

BACKGROUND OF THE INVENTION

1. Field of the Invention

A catheter device primarily designed for the catherization of a predetermined blood vessel during the process of hemodialysis and structured to have the operating characteristics which include continuous flow of blood to and from the vessel through fluid segregated flow paths both positionable into the predetermined blood vessel by a single puncture.

2. Description of the Prior Art

At the present time it is well accepted medical practice in the performance of both emergency and cronic hemodialysis to utilize two separate catheters in the blood vessel or vessels being catherized. Each of the catheters are placed separately requiring at least two "sticks" or punctures of the body of the patient. These plurality of punctures required in the placement of the separate catheters is naturally accompanied by the usual pain and discomfort to the patient. Placement of the individual catheters is accomplished commonly by the Seldinger technique.

The Seldinger technique involves the perforation of a vein with a hollow needle. A flexible wire is then threaded through the needle and up the vein. The needle is withdrawn over the wire and a plastic flexible catheter is slipped down over the wire using it as a guide for proper placement of the catheter on the interior of the blood vessel. A second catheter is then inserted in this same manner thereby requiring placement of two needles in the patient with the attendant pain as set forth above. Due to the fact that the second catheter is almost always more difficult to place than the first, especially when the catheters are placed at different levels in the same blood vessel, it is common for more than two sticks or perforations of the patient to be required. In addition, when placing the second catheter in the same blood vessel as the first catheter in relative adjacent location actual placement of the catheter is accomplished by the manipulation in somewhat of a twisting fashion. Frequently, this causes fouling or entanglement of the two catheters.

Accordingly, it can readily be seen that a single catheter device having equal or superior performance characteristics as that of two separate catheters would be highly desirable due to the reduction in pain and discomfort to the patient undergoing the dialysis treatment. Accordingly, the use of a coaxial flow catheter incorporating essentially inner and outer catheter tubes would naturally be more desirable since proper positioning of such a device could be accomplished with obviously less discomfort to the patient.

In fact, coaxial flow devices per se are available in the prior art for use in generally similar medical procedures.

For instance, the patent to Bennett, U.S. Pat. No. 3,670,729 is directed to a tranfusion needle wherein an inner elongated tube 22 is used to pass blood into a predetermined vessel in the human body. An outer, coaxial and concentrically arranged tube relative to the inner tube, is provided with pores in the external surface thereof so as to provide a cleansing or disinfecting fluid to the area of the puncture of the transfusion needle at the point of entry of the body. However, this structure is not designed to accomplish flow in the inner and outer tubes in opposite directions to accomplish delivery of blood to and from a blood vessel as required in hemodialysis treatment.

In the area of dialysis medical equipment has been developed which utilizes only a single catheter wherein blood is alternatively forced to and from the blood vessel of the body in which the catheter is placed through the utilization of relatively complex machinery which operates at questionable efficiency and relative great expense. Prior art devices of this type are generally represented in the patents to Lange, U.S. Pat. No. 3,520,298, and Kopp, U.S. Pat. No. 3,756,234.

However, as set forth above, devices generally representative of this type are frequently, due to their complexity, expensive to maintain and procure as well as being noisy in operation thereby adding to the discomfort of the patient during treatment.

Other devices known in the prior art which are designed for the transfer of fluid to and from the body are represented in the patent to Hsi Hu, U.S. Pat. No. 2,564,977. While devices of this type are not specifically directed to dialysis treatment they are directed to the transfer on a continuous or alternating basis of fluid to and from predetermined portions of the human body.

In spite of the existence of prior art and present commercially available devices there is still a need for medical apparatus in the form of a catheter device capable of efficient operation with minimum discomfort and pain to the patient. Ideally, such a device would be capable of continuous and concurrent flow of blood both to and from the patient.

SUMMARY OF THE INVENTION

This invention relates to a catheter device including a hub assembly interconnected to a tube means including an outer and inner tube substantially, coaxially and concentrically arranged relative to one another. The hub assembly has at least two fluid conduits disposed in spaced and fluid segregated relation to one another wherein each of the two conduits are interconnected in fluid communication to one of the inner or outer tube elements.

Accordingly, a first fluid flow path is at least partially defined by the interconnected outer tube element and one of the two conduits. A second fluid flow path may be at least partially defined by interconnection between the inner tube element and the other of the two fluid conduits. Each of these first and second fluid flow paths are disposed in segregated relation to the fluid flow therein.

Each of the fluid conduits are further defined and/or include free ends disposed opposite to their point of connection or junction to the outer and inner tube elements. The positive and negative sources of fluid flow may be generally defined within the applicable dialysis equipment with which the catheter device of the subject invention is connected. Therefore, the positive and negative source of fluid flow per se does not form part of the present invention but merely defines the activating force which causes blood to flow both from and to a predetermined blood vessel in which the catheter device is mounted. More specifically, in the preferred embodiment of the present invention both the positive and negative source of fluid flow is a continuous and concurrently activated source so as to define a continuous and concurrent flow of blood to the predetermined blood vessel in which the catheter device is mounted. With reference to the tube means itself, the inner tube comprises a substantially greater length and includes an aperture at the free end thereof through which blood is directed into the predetermined blood vessel. The outer tube element, on the other hand is of shorter length and terminates a spaced distance from the end or extremity of the inner tube at which is located the aperture noted above. Therefore, placement of the inner and outer tube portion of the catheter within the predetermined blood vessel serves to dispose the aperture extremity of the inner tube "downstream" of the outer tube relative to the direction of blood flow in the blood vessel. The outer tube may comprise one or more pores formed in its wall wherein such pores are located "upstream" of the apertured extremity of the inner tube.

Therefore, in actual operation "fresh" or processed blood from the dialysis machine enters the blood vessel downstream of the point where the untreated blood is withdrawn from the same blood vessel. Due to the fact that the blood will continue to flow in the same direction, this placement of the inner and outer tube at different levels from one another will prevent the passing of the treated blood into the outer tube element which is located upstream of its point of entry. Obviously the treated blood will be prevented from flowing upstream against the normal direction of flow of the blood traveling through the blood vessel in which the catheter device is mounted.

With reference to the hub assembly, a preferred embodiment of the present invention comprises its formation in what may be termed a "butterfly" configuration. More specifically, the hub assembly includes two hub portions each having a corresponding configuration and each hub portion including conduit portions which, when the hub portions are arranged in mated, engaging relation to one another define the two fluid conduits set forth above. The two hub portions are joined along a junction line disposed along the substantial center of the hub means such that the joined hub portions define a substantially symetrical configuration.

In one embodiment of the present invention the junction line may comprise a hinge line such that folding of one hub portion relative to this hinge line into mating engagement with the other hub portion will serve to assemble the hub means into closed, sealed operative relation to one another. Joining means in the form of an outwardly extending flange at least along a portion of the periphery of each hub portion may be disposed in mating relation to one another and sealed together by means of an ultrasonic weld or other acceptable sealing means to define the hub assembly in its closed operative position.

Other structural features of the hub assembly include socket means integrally formed therein and correspondingly configured to have mounting means which are attached to the inner and outer tube elements such that mounting of the tube elements will be facilitated by positioning of the joining within the socket means thereby minimizing the possibility of error during assembly.

This invention accordingly comprises the features of construction, combination of elements and arrangement of parts which will be exemplified in the construction hereinafter set forth and the scope of the invention will be indicated in the claims.

BRIEF DESCRIPTION OF THE DRAWINGS

For a fuller understanding of the nature and the objects of the invention, reference should be had to the following detailed description taken in connection with the accompanying drawings in which:

FIG. 2 is a front view of the interior of one hub portion in partial section and cutaway of the subject catheter device.

FIG. 3 is a detailed view of the interior of the hub assembly.

FIG. 4 is a detailed view in partial cross section of the tube means including outer and inner tube elements.

FIG. 5 is a sectional view along line 5—5 of FIG. 3 showing the interior of one hub portion of the hub assembly.

FIG. 6 is a sectional view along line 6—6 of FIG. 1 showing the relationship of two hub assemblies in closed mating relation to one another to form the hub means.

Similar reference characters refer to similar parts throughout the several views of the drawings.

DETAILED DESCRIPTION

Figure 1:
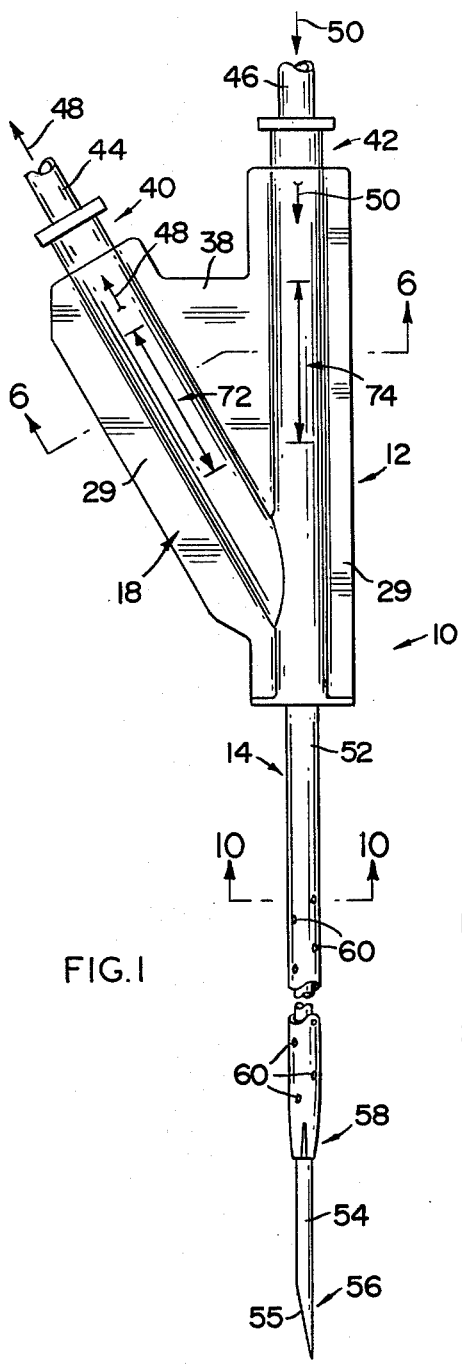
FIG. 1 is a front plan view of the catheter device of the present invention.
Figure 7:
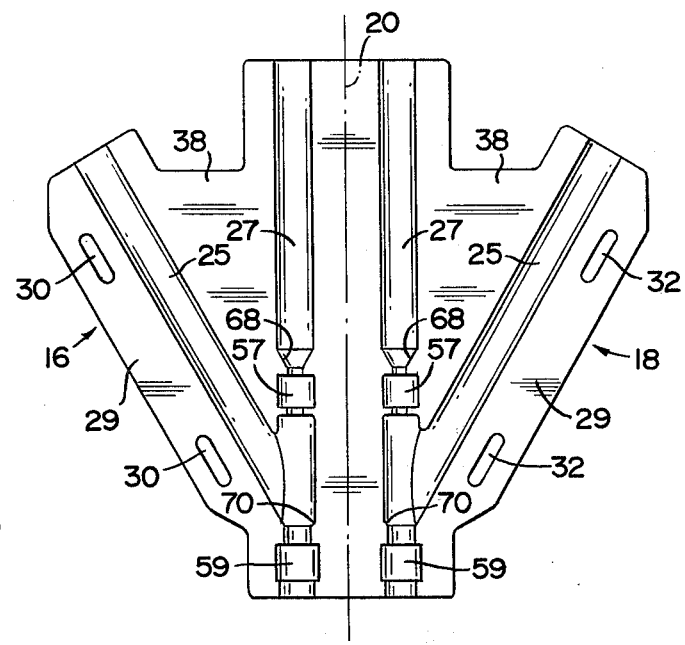
FIG. 7 is a detailed view showing the interior of the hub assembly and the relationship of the two joined hub portions forming the hub assembly.

As shown in FIGS. 1 and 2 the subject invention relates to a catheter device generally indicated as 10 which includes a hub assembly generally indicated as 12 having tube means 14 attached thereto in a manner which will be set forth in greater detail hereinafter.

Figure 8:
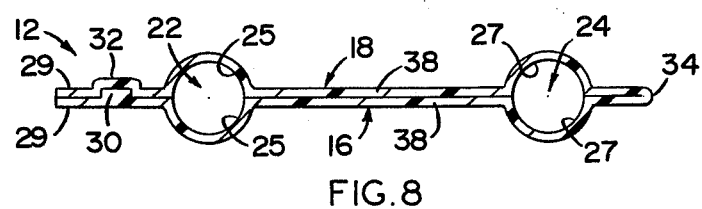
FIG. 8 is a sectional view showing the alignment means and general relation of the hub portion to one another when in mating relation.

With reference to FIGS. 3, 5, 6, 7 and 8, the hub assembly 12 comprises at least two hub portions 16 and 18 which may be integrally connected to one another along a common junction line 20. At least two fluid conduits 22 and 24 (FIGS. 6 and 8) are formed on the interior of the hub assembly 12. More particularly with reference to FIG. 7 at least one and preferably both of the hub portions 16 and 18 have integrally formed therein conduit portions 25 and 27. Each of these conduit portions mentioned are disposed to at least partially define respective conduits 22 and 24 as shown in FIGS. 6 and 8. Joining means in the form of flanges 29 extend outwardly about at least a portion of the periphery of each hub portion 16 and 18. These flange means are correspondingly positioned so as to be brought into mating engagement with one another (FIG. 8). In addition, alignment means in the form of tongue and socket elements 30 and 32, respectively, are integrally formed in the peripheral flanges 29. These tongue and socket elements 30 and 32, respectively, are correspondingly positioned on their respective flanges 29 so that when brought into locking, mating engagement as shown in FIG. 8 the remaining portions of the hub assembly, namely conduit portions 25 and 27 will be properly aligned so as to accurately form the individual fluid conduits 22 and 24. One embodiment of the hub assembly includes the junction line 20 defining a hinge line generally indicated as 34 wherein the two hub portions 16 and 18 may be folded about hinge line 34 relative to one another into mating engagement, again as shown in FIG. 8.

When the hub portions 16 and 18 are sealed flanges 29 are affixedly attached to one another and may be permanently affixed into sealing engagement by means of an ultrasonic seal or other applicable means for securing the two hub portions 16 and 18 together.

As shown in FIGS. 1 and 2 exterior of the hub assembly may further include a web area 38 which essentially is disposed in interconnecting relation to the two fluid conduits or at least the exterior wall portions thereof. This web portion may be used to have placed thereon certain indicia, proper markings, instructions or advertisements. With reference to FIGS. 1 and 2 the free ends of each fluid conduit generally indicated as 40 and 42 have formed therein or made a part thereof luer-type fittings. While luer fittings are preferred in this embodiment of the present invention any other applicable means can be used to interconnect a source of fluid flow to the free ends of the fluid conduits. More specifically, a negative source of fluid flow is connected to the free end or luer fitting generally indicated as 40 to one of the fluid conduits. Such a negative source of fluid flow is not specifically shown by generally represented connection 44. Similarly, a positive source of fluid flow is connected to the luer fitting and/or free end of the fluid conduit 24 and is generally represented in broken lines as connected 46 but is not specifically shown. As will be explained in greater detail hereinafter the continuous source of negative fluid pressure causes the blood to pass up through the fluid conduit 22 from the tube means 14 simultaneously to the positive source of fluid pressure causing the blood to return down from the dialysis machine through fluid conduit 24 and the tube means 14. The respective directions of fluid flow are represented by directional arrows 48 and 50 (FIG. 2).

With reference primarily to FIGS. 1, 2, 4 and 10 the tube means 14 comprises a plurality of tube elements including an outer tube element 52 and an inner tube element 54 arranged in coaxial, concentric relation to one another. The inner tube element 54 has a linear dimension somewhat greater than that of the outer tube 52 such that its free end generally indicated as 56 extends beyond the free end 58 of the outer tube 52. Further, the free end 56 includes an aperture 55 formed therein so as to allow blood to pass from aperture 55 from the interior of inner tube 54 which is interconnected to the interior of fluid conduit 24. Outer tube element 52 has its terminal portion 58 sealed to the outer surface of the tube element as shown. A plurality of pores 60 are formed in the wall of the outer tube 52 so as to draw blood through these pores into the interior of the outer tube 52 and up through conduit 24 formed by the conduit portion 25.

Accordingly, interconnection of outer tube element 52 with fluid conduit 54 defines a first path of fluid flow which is connected to the negative source of fluid pressure by means of connector 44 in order to draw the blood from the interior of a blood vessel in which the catheter is placed along this first path of fluid flow to the dialysis equipment connected to the hub assembly. Similarly, a second path of fluid flow is difined by the second fluid conduit 24 and the interconnected inner tube 54. As indicated by directional arrow 50 blood is forced down into the blood vessel out of aperture 59 by virture of this second path of fluid flow being connected to the positive source of fluid pressure through connector means 46. Again by virtue of the fact that the negative and positive sources of fluid pressure represented by 44 and 46, respectively, are continuous in nature, there is established a continuous flow into and out of the blood vessel in which the catheter device is mounted such that blood is drawn from the blood vessel through the outer tube 52 on a continuous basis simultaneously to blood being delivered back into the blood vessel through the inner tube 54.

Another embodiment of the present invention includes the means of joining or mounting the inner and outer tube elements 54 and 52 to the hub assembly. With reference to FIGS. 2, 3, 4 and 5, each of the hub portions 16 and 18 are provided with socket means 57 and 59. These socket means are correspondingly dimensioned and configured to the dimensions and configurations of the mounting means in the form of protruding extensions 62 and 64 integrally formed or otherwise separately attached to the upper end of the inner and outer elements 54 and 52, respectively. Accordingly, by virtue of this structure ease and accuracy of assembly is insured in that the operator merely must place the protrusions 62 and 64 in the properly designated socket means 57 and 59 and provide whatever sealing facility thereto which have been predetermined. The various socket portions (as clearly shown in FIG. 7) which comprise the socket means 57 and 59 may be integrally formed in one or both of the hub portions 16 and 18 whereby the entire socket means 57 and 59 are formed upon mating engagement of the two hub portions 16 and 18. Each of the socket means 57 and 59 are arranged in aligned, substantially coaxial relation to one another wherein socket means 57 substantially defines the junction or point of interconnection between the inner tube 54 and the fluid conduit 24 in a manner which segregates the fluid flowing therein from the fluid flow in the first fluid flow path defined by the outer tube element 52 and the fluid conduit 22.

Similarly socket means 59 defines the junction or the point of interconnection between fluid conduit 22 and the outer tube 52. The interconnection of fluid conduit 22 and outer tube 52 defines the first fluid flow path as set forth above. By virtue of the interconnections as set forth above it is clear that the fluid flow between the first fluid flow path and the second fluid flow path are clearly segregated and in fact travel in opposite directions on a continuous basis once the dialysis machine which is attached to the catheter device 10 of the subject invention is activated.

Figure 9:
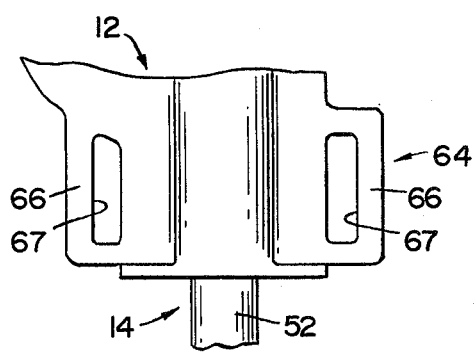
FIG. 9 is a detailed view of a connector means which may be included in one embodiment of the present invention.
Figure 10:
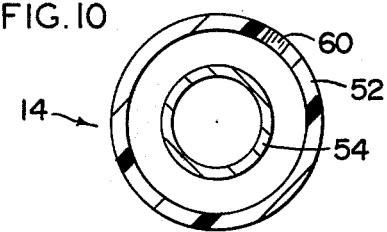
FIG. 10 is a sectional view along line 10—10 of FIG. 1 showing the concentric relation of the outer and inner tube elements relative to one another.

Another embodiment of the present invention is shown in detail in FIG. 9 and comprises a connector means generally indicated as 64 mounted on the exterior of the device which may be, in the embodiment shown, the exterior of the hub assembly 12. The connector may comprise one or more apertured ear elements 66 including aperture 67 formed therein. By virtue of this arrangement a strap or like connector (not shown) can be threaded through the aperture 67 and attached to the leg, limb or other portion of the body of the patient in whom the catheter device is mounted. This connector means facilitates comfortable placement of the catheter device on the patient and also reduces the possibility of inadvertent movement or displacement of the catheter device upon movement of the patient.

Yet another structural feature of the present invention comprises fluid directing means including tapered or angular portion 68 disposed immediately upstream and/or adjacent to at least one junction or point of interconnection of a tube element. With specific reference to FIGS. 2 and 3 the fluid directing means in the form of tapered portion 68 is located immediately upstream of socket means 57 of the point of interconnection of the inner tube 54 with the fluid conduit 24. This tapered portion serves to direct the fluid directly into the inner tube 54 from the fluid conduit 24 in a manner which serves to eliminate or substantially reduce any unwanted turbulence in the blood as it passes along the fluid flow path defined by a particular fluid conduit and interconnected tube element. Similarly, tapered portion 70 is provided immediately downstream of the point of interconnection of the outer tube 52 with the fluid conduit 22. This tapered portion 70 also comprises a part of the fluid directing means again serves to reduce the turbulence of the blood as it flows along the fluid flow path defined by the fluid conduit 22 and the outer tube 52 especially as it exits this outer tube 52.

With reference to FIG. 1 the present invention comprises yet another structural feature which includes a flow restrictor means generally indicated as 72 and 74. More specifically these flow restrictor means comprise flexible or weakened portions in the wall of the respective fluid conduits 22 and 24. Provision of these flexible or weakened portions allows for a clamping off of the respective fluid conduits and therefore a restriction of fluid flow within these conduits. Such restriction of flow is advantageous when initially applying or interconnecting the catheter device itself to the proper tubing of the dialysis facility and/or more specifically the sources of negative and positive fluid pressure. Once the inner and outer tubes are placed within the vessel and immediately prior to either of the fluid conduits 22 and 24 being connected to their sources of fluid pressure, the blood within the vessel will have a tendency to flow up through the inner and outer tubes into the fluid conduits and exit from the free ends 40 and 42 of the respective fluid conduits 22 and 24. Loss of blood can result unless flow through the respective fluid conduits is restricted through a clamping of the flow restrictor means 72 and 74 either manually or through conventional clamping devices.

It will thus be seen that the objects made apparent from the preceding description, are efficiently attained and since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Now that the invention has been described,

What is claimed is:

1. A catheter device for the catherization of predetermined blood vessels required during hemodialysis, said catheter device comprising: a hub means including at least two fluid conduits disposed in spaced, separated relation to one another; tube means connected to said hub means and including at least an inner tube element and an outer tube element disposed in concentric relation to one another, each of said tube elements connected in fluid communicating relation to one of said two fluid conduits, said hub means comprising socket means formed in said hub means, mounting means formed on said tube means and comprising at least in part a substantially corresponding configuration as said socket means; said mounting means disposed in mounted engagement with said socket means on the interior of said hub means; a first path of fluid flow defined by the interconnected outer tube of one of said fluid conduits; a second fluid flow path defined by the interconnected inner tube element and the other of said fluid conduits, said first and second fluid flow paths disposed in segregated relation to one another; said first and second fluid flow paths interconnected to a continuous negative and positive source of fluid pressure, whereby a continuous flow of blood simultaneously travels from and to the predetermined blood vessel upon activation of the positive and negative source of fluid flow.

2. A catheter device as in claim 1 wherein said outer tube element extends along a predetermined length of said inner tube element, said outer tube element having pore means formed therein, said inner tube element being apertured at least at the free end thereof, whereby fluid flow passes from and to the predetermined blood vessel through said outer and inner tube elements respectively.

3. A catheter device as in claim 1 wherein each of said two fluid conduits include a free end, each of said free ends of said two fluid conduits including a luer fitting.

4. A catheter device as in claim 1 wherein said socket means comprises at least two socket elements disposed in aligned, substantially coaxial relation to one another, each of said socket elements disposed along and at least partially defining one of said first or second fluid flow paths.

5. A catheter device as in claim 4 wherein one of said socket elements substantially defines the junction of each of said inner and outer tube elements with each of respective ones of said fluid conduits, said socket means disposed in fluid flow segregated relation to one another.

6. A catheter device as in claim 4 further comprising fluid directing means disposed in upstream, fluid guiding relation to at least one of said socket elements, whereby turbulence of flow on the interior of said hub means in reduced.

7. A catheter device as in claim 1 further comprising flow restrictor means mounted on said hub means and disposed in flow interruptive relation to at least one of said first and second fluid flow paths.

8. A catheter device as in claim 7 wherein said flow restrictor means comprises flexible wall portions integrally formed in the wall of said hub means in corresponding relation to at least one of said two fluid conduits.

9. A catheter device as in claim 7 wherein said flow restrictor means comprises flexible wall portions formed in the wall of said hub means in corresponding relation to both of said two fluid conduits.

10. A catheter device as in claim 1 further comprising connector means mounted on the exterior of said catheter device and configured to dispose said catheter device in attached relation to the patient utilizing said catheter device.

11. A catheter device as in claim 1 wherein said hub means comprises two hub portions integrally attached to one another, each of said hub portions comprising conduit portions which themselves are correspondingly disposed and configured so as to at least partially define said two fluid conduits when said hub portions are disposed in mating engagement with one another, said hub means having a substantially symetrical configuration relative to the junction of said two hub portions defining said hub means.

12. A catheter device as in claim 11 wherein said junction disposed in interconnecting relation to said two hub portions comprises a hinge line about which one of said hub portions may be rotated relative to the other of said hub portions so as to bring said two hub portions into mating engagement with one another.

13. A catheter device for the catherization of predetermined blood vessels required during hemodialysis, said catheter device comprising: a hub means including at least two fluid conduits disposed in spaced, separated relation to one another; tube means connected to said hub means and including at least an inner tube element and an outer tube element disposed in concentric relation to one another, each of said tube elements connected in fluid communicating relation to one of said two fluid conduits, said hub means comprising at least two hub portions, at least one of said hub portions including conduit portions formed therein and being substantially correspondingly configured and disposed to at least partially define said two fluid conduits, said two hub portions disposed in engageable, mating relation to one another, whereby said hub means is formed upon the mating engagement of said hub portions; a first path of fluid flow defined by the interconnected outer tube one of said fluid conduits; a second fluid flow path defined by the interconnected inner tube element and the outer of said fluid conduits, said first and second fluid flow paths disposed in segregated relation to one another; said first and second fluid flow paths interconnected to a continuous negative and positive source of fluid pressure, whereby a continuous flow of blood simultaneously travels from and to the predetermined blood vessel upon activation of the positive and negative source of fluid flow.

14. A catheter device as in claim 13 wherein each of said hub portions include substantially correspondingly configured conduit portions, said conduit portions at least partially defining said two fluid conduits.

15. A catheter device as in claim 13 wherein said hub portions each comprise joining means including an outwardly extending flange along at least a portion of the periphery of each of said hub portions, said flanges of each hub portion disposed in substantially corresponding, mating engagement with one another when said hub means is in its assembled position.

16. A catheter device as in claim 15 further comprising alignment means formed in each of said flange of each hub portion and positioned to dispose the corresponding conduit portions of said hub means in predetermined relation to one another upon the mating engagement of said hub portions.

17. A catheter device as in claim 15 wherein said flanges of both hub portions are sealed together by ultrasonic weld.

* * * * *